United States Patent [19]

Chia-ching

[11] Patent Number: 5,466,366
[45] Date of Patent: Nov. 14, 1995

[54] WATER TEMPERATURE AND CONDUCTIVITY DETECTOR FOR REVERSE-OSMOSIS WATER PURIFIER SYSTEMS

[75] Inventor: Huang Chia-ching, Hsinchu City, Taiwan

[73] Assignee: New Gulf Measurement Instrument Ltd. Company, Hsinchu City, Taiwan

[21] Appl. No.: 189,634

[22] Filed: Feb. 1, 1994

[51] Int. Cl.⁶ ............................ B01D 61/10; B01D 17/12
[52] U.S. Cl. ..................... 210/85; 204/409; 210/96.2; 324/441; 324/446
[58] Field of Search .............. 210/85, 96.1, 96.2, 210/149, 742, 746; 324/439, 441, 446, 450; 204/408, 409

[56] References Cited

U.S. PATENT DOCUMENTS

| | | | |
|---|---|---|---|
| 2,505,936 | 5/1950 | Behn | 324/441 |
| 2,611,007 | 9/1952 | Cade et al. | 324/441 |
| 2,611,113 | 9/1952 | Cade et al. | 324/441 |
| 2,616,949 | 11/1952 | Cade | 324/441 |
| 3,471,393 | 10/1969 | Ingruber | 324/441 |
| 4,563,272 | 1/1986 | Yoshida et al. | 210/96.1 |
| 5,096,574 | 3/1992 | Birdsong et al. | 210/96.2 |

*Primary Examiner*—Joseph W. Drodge

[57] ABSTRACT

A water temperature and conductivity detector includes a detector unit, a cup-shaped bottom shell, and a socket connector having a top end connected to the detector unit, a bottom end connected to the cup-shaped bottom shell, a water inlet connected to a water supply system, and a water outlet connected to a reverse-osmosis water purifier system, the detector unit having two electrodes projected into the cup-shaped bottom shell to detect the conductivity of water passing from the water supply system to the reverse-osmosis water purifier system, and a heat sensitive resistor to compensate the temperature of water passing through the detector.

4 Claims, 3 Drawing Sheets

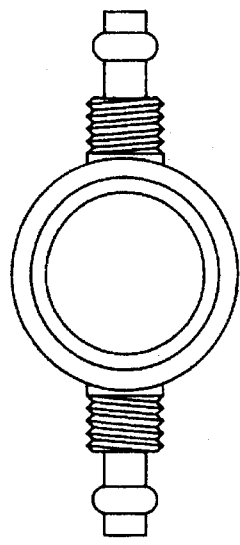
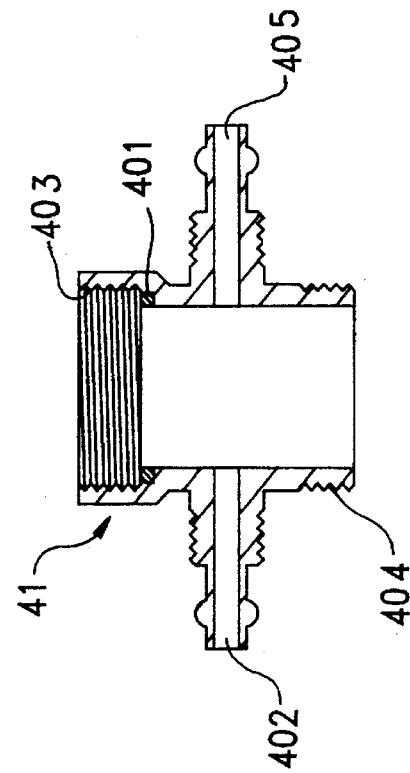
FIG. 4B
FIG. 4A
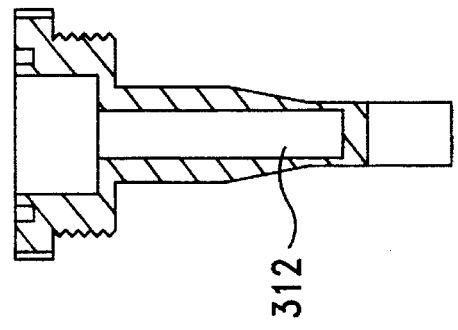
FIG. 3B
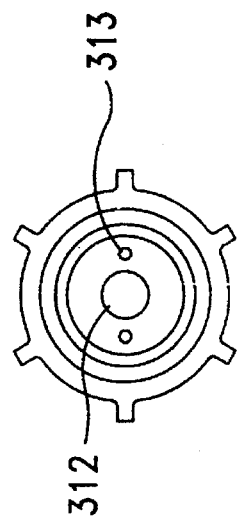
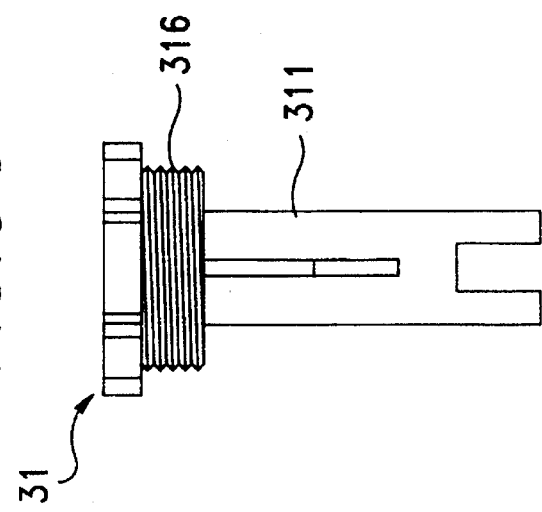
FIG. 3C
FIG. 3A

WATER TEMPERATURE AND CONDUCTIVITY DETECTOR FOR REVERSE-OSMOSIS WATER PURIFIER SYSTEMS

BACKGROUND OF THE INVENTION

The present invention relates to a water temperature and conductivity detector, and more particularly to such a water temperature and conductivity detector for detecting the temperature and conductivity of water passing through a reverse-osmosis water purifier system.

Various water filters and purifier systems have been disclosed, and have appeared on the market. These systems include reverse-osmosis water purifier systems. A home use reverse-osmosis water purifier system, as shown in FIG. 1, comprises a high pressure pump G controlled to pump water through a reverse-osmosis cylinder G1. The output port of the reverse-osmosis cylinder is connected to a water tap from which purified water is obtained. In order to obtain high quality pure water, the conductivity and temperature of the water obtained from the reverse-osmosis cylinder must be inspected and controlled. FIG. 2 shows a water conductivity detector for a reverse-osmosis water purifier system according to the prior art, which comprises a detector drum A1 having a water intake port A at the top connected to the reverse-osmosis water purifier system through a branch pipe and a water drain hole at the bottom for drawing off water after each test. This structure of water conductivity detector is not suitable for home use because water must be regularly renewed for a new test. As the whole electrodes A2 are not insulated, the water level in the detector drum will affect the result of detection. Furthermore, this structure of detector does not detect the temperature of water. As temperature affects the working efficiency of a reverse-osmosis water purifier, it is important to constantly detect the temperature of water passing through or running out of a reverse-osmosis water purifier.

SUMMARY OF THE INVENTION

The present invention has been accomplished under the aforesaid circumstances. It is therefore an object of the present invention to provide a water temperature and conductivity detector for a reverse-osmosis water purifier system which automatically and constantly detects the temperature and conductivity of water passing through. It is another object of the present invention to provide a water temperature and conductivity detector for a reverse-osmosis water purifier system which automatically compensates the temperature of water passing through. It is still another object of the present invention to provide a water temperature and conductivity detector for a reverse-osmosis water purifier system which is easy to assemble and convenient to install. It is still another object of the present invention to provide a water temperature and conductivity detector for a reverse-osmosis water purifier system which is detachable for easy wash.

According to the preferred embodiment of the present invention, the water temperature and conductivity detector comprises a detector unit, a cup-shaped bottom shell, and a socket connector having a top end connected to the detector unit through a screw joint, a bottom end connected to the cup-shaped bottom shell through a screw joint, a water inlet tube connected to a water supply system, and a water outlet tube connected to a reverse-osmosis water purifier system. The detector unit comprises two insulated electrodes having a respective bare tip projected into the cup-shaped bottom shell to detect the conductivity of water passing from the water supply system to the reverse-osmosis water purifier system, and a heat sensitive resistor received within a countersunk hole thereof to detect and compensate the temperature of water passing through the detector.

BRIEF DESCRIPTION OF THE DRAWINGS

FIGS. 3A, 3B, and 3C show the views of the detector unit of a water temperature and conductivity detector according to the preferred embodiment of the present invention;

FIGS. 4A and 4B show the views of the socket connector of the water temperature and conductivity detector of the preferred embodiment of the present invention;

DETAILED DESCRIPTION OF THE PREFERRED EMBODIMENT

Figure 1:
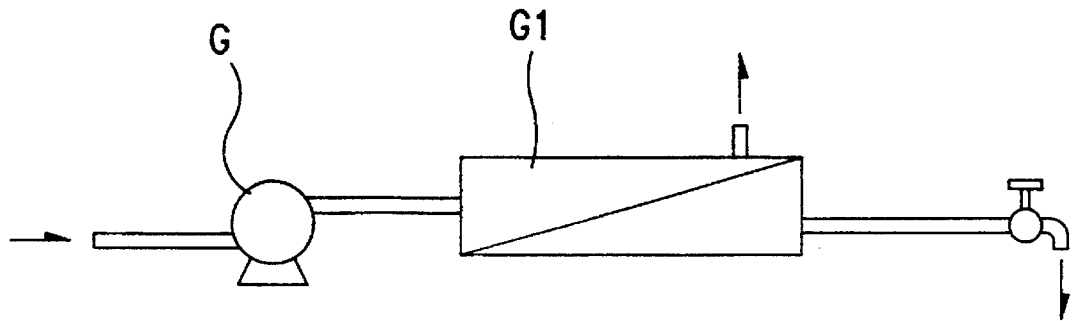
FIG. 1 illustrates a conventional reverse-osmosis water purifier system.
Figure 2:
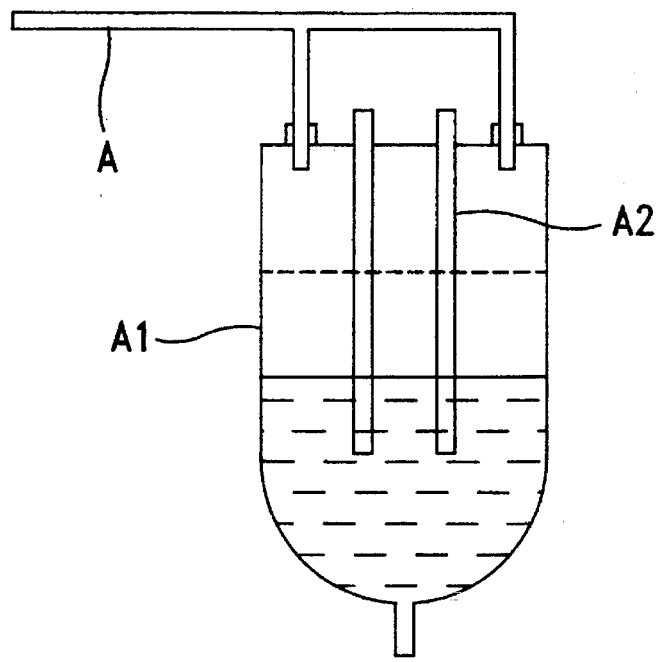
FIG. 2 is a plan view of a water temperature and conductivity detector for a reverse-osmosis water purifier system according to the prior art.

Referring to FIGS. 3A, 3B, 3C, 4A, 4B, 5A and 5B, a water temperature and conductivity detector in accordance with the present invention is generally comprised of a detector unit 31, a socket connector 41, and a cup-shaped bottom shell 51. The detector unit 31 is comprised of a stepped cylinder 311 made of plastics through an injection molding process, having a countersunk hole 312 in the longitudinal direction, two longitudinal through holes 313 through the length of the stepped cylinder 311 in parallel with the countersunk hole 312, and an outer thread 316 near the top thereof. A heat sensitive resistor (not shown) is installed in the countersunk hole 312 to compensate the temperature of water passing through the water temperature and conductivity detector. Two electrodes 314 (see FIG. 6) are fastened within the detector unit 31 and respectively extended out of the longitudinal through holes 313 for detecting the conductivity of water passing through. The socket connector 41 is made of plastics through an injection molding process, having an inner thread 403 at the top threaded onto the outer thread 316 on the detector unit 31 and then sealed with a water seal ring 401, an outer thread 404 at the bottom for mounting the cup-shaped bottom shell 51, a water inlet tube 402 at one side connected to the water outlet port 60 of a water supply system, a water outlet tube 405 connected to the water inlet port 61 of a reverse-osmosis water purifier system. The cup-shaped bottom shell 51 comprises an inner thread 511 around the inside wall of the top orifice 512 thereof and screwed up with the outer thread 404 on the socket connector 41 and then sealed with a water seal ring 510.

Figure 6:
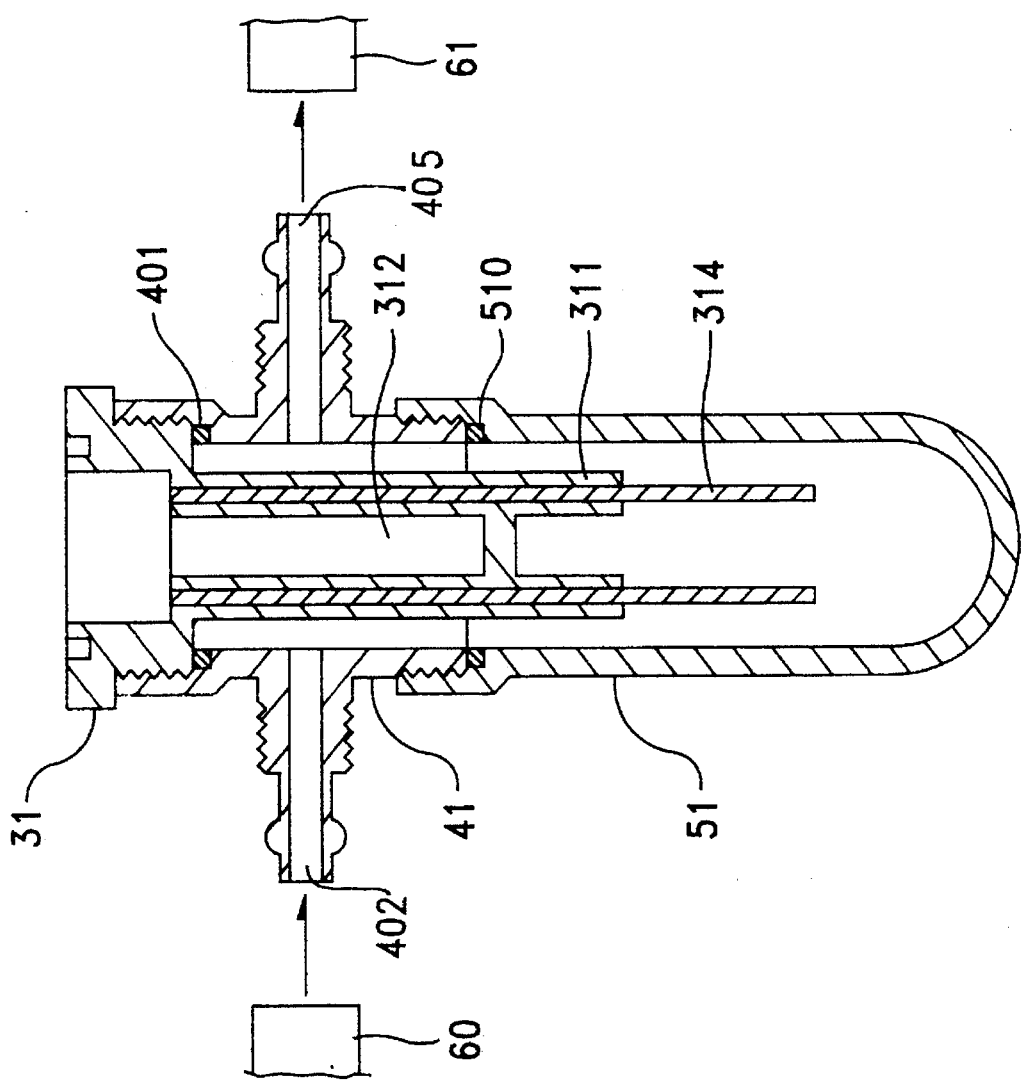
FIG. 6 is an installed view of the water temperature and conductivity detector of the preferred embodiment of the present invention.
Figures 5A, 5B:
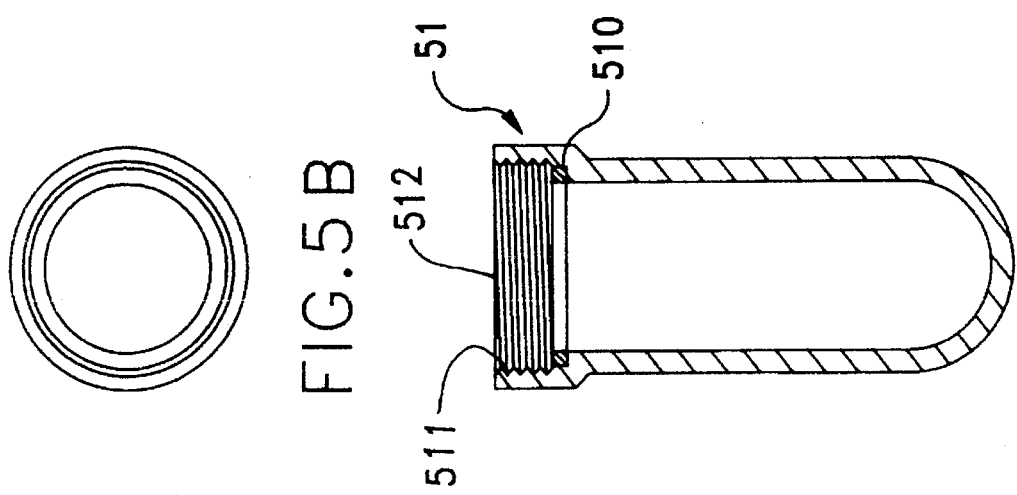
FIGS. 5A and 5B show the views of the cup-shaped bottom shell of the water temperature and conductivity detector of the preferred embodiment of the present invention.

When assembled, as shown in FIG. 6, the electrodes 314 are respectively insulated, having a respective bare tip projected into the space within the cup-shaped bottom shell 51 to detect the conductivity of water passing from the water outlet port 60 of the water supply system to water inlet port 61 of the reverse-osmosis water purifier system. The bottom end of the electrodes 314 must be disposed at least 1 cm (one centimeter) below the elevation of the water outlet port 60 of the water supply system. Therefore, the electrodes 314 effectively detect the temperature of water passing through. Further, the lead wires (not shown) of the electrodes 314 and the heat sensitive resistor may be connected to an indicator instrument (electronic display device) to show the detections.

While only one embodiment of the present invention has been shown and described, it will be understood that various modifications and changes could be made without departing from the spirit and scope of the invention.

What is claimed is:

1. A water temperature and conductivity detector comprising:
    a detector unit, which comprises a head and a stepped cylinder extended from said head and having a heat sensitive resistor received in a hole thereof and two electrodes extended out of a bottom end thereof, said stepped cylinder comprising an upper cylinder section and a lower cylinder section extended from said upper cylinder section, the outer diameter of said lower cylinder section being smaller than that of said upper cylinder section;
    a socket connector fastened around said upper cylinder section of said stepped cylinder of said detector unit and spaced from said lower cylinder section, said socket connector having a water inlet tube and a water outlet tube respectively constructed and arranged for connecting to a water outlet port of a water supply system and a water inlet port of a reverse-osmosis water purifier system;
    a cup-shaped bottom shell having a top orifice fastened around the bottom of said socket connector; and
    wherein when water from said water supply system flows through said water inlet tube of said socket connector and a space defined within said cup-shaped bottom shell and said water outlet tube of said socket connector to said reverse-osmosis water purifier system, the conductivity of the flow of water is detected by said electrodes, and the temperature is compensated by said heat sensitive resistor.

2. The detector of claim 1 wherein said socket connector is made of plastics through an injection molding process, wherein an inner thread at the top of said socket connector is screwed with an outer thread of said stepped cylinder of said detector unit and then sealed with a water seal ring, and an outer thread at the bottom of said socket connector is threaded into an outer thread within said top orifice of said cup-shaped bottom shell and then sealed with a water seal ring.

3. The detector of claim 1 wherein said detector unit and said cup-shaped bottom shell are respectively made of plastics through an injection molding process.

4. The detector of claim 1 wherein said electrodes are respectively insulated and mounted in respective through holes on said stepped cylinder of said detector unit, and a respective bare tip is extended out of said stepped cylinder at an elevation at least 1 cm below the elevation of said water outlet port of said water supply system.

* * * * *